US00PP08556P

United States Patent [19]

Bennett, deceased et al.

[11] Patent Number: Plant 8,556

[45] Date of Patent: Jan. 25, 1994

[54] MINIATURE ROSE PLANT NAMED 'ELIZABETH ABLER'

[76] Inventors: Cecilia L. D. Bennett, deceased, late of Chula Vista, Calif., by Susan Mae O'Brien, special administrator; Susan M. O'Brien, 489 Minot Ave., Chula Vista, Calif. 91910

[21] Appl. No.: 999,366

[22] Filed: Dec. 31, 1992

[51] Int. Cl.[5] ..... A01H 5/00

[52] U.S. Cl. ..... Plt./10

[58] Field of Search ..... Plt. 9, 10

*Primary Examiner*—James R. Feyrer

[57] ABSTRACT

The subject of the present disclosure is a new and distinct variety of miniature rose plant, named 'Elizabeth Abler' which is characterized by microminiature buds and blooms ranging from near Currant Red to near Rose Red with inner petals ranging from near Crimson to near Rose Madder. Blooms of this rose are usually borne one to a stem with hybrid tea form. The bush is compact, well-branched and prolific in its production of blooms.

1 Drawing Sheet

The present invention relates to a new and distinct variety of a hardy, dwarf, bush plant of the miniature class; the variety being primarily characterized as medium red.

The variety is further characterized by:

The small hybrid tea-type form blooms are borne one to a stem and held very erect and well above the foliage.

The plant ranges in a height from 8 to 12 inches (20 to 30 cm). The canes are sturdy and erect with moderate branching and medium to heavy foliage covering. The plant is a heavy bloomer that does well either in the greenhouse or outdoors.

The plant has good growth habits, well-shaped and attractive, bearing numerous leaflets of average size. I have found this variety to be easily asexually reproduced from cuttings as performed in the nursery located at 489 Minot Avenue, Chula Vista, Calif.

The seed parent was an unnamed seedling rose (Christian Dior×Brian Lee), and the pollen parent is unknown but presumed to be the same unnamed seedling, as no artificial cross-pollination had occurred on this plant, before the hip was formed. It differs from its unnamed seed parent and the rose cultivars that created the seed parent in the following ways. Elizabeth Abler is a medium red miniature rose with extremely small blooms, foliage and growth habit; whereas the unnamed seed parent has much larger blooms, foliage and growth habit, more typical of a floribunda sized rose; and the color is dark red. Christian Dior (U.S. Plant Pat. No. 1,943) is a large hybrid tea rose with bloom size of 10 to 12 cm; whereas Elizabeth Abler has blooms of less than 2 cm in diameter. Brian Lee (U.S. Pat. No. 6,789) is a miniature rose with a bloom size of 30 to 40 mm. It has been various reclassified by the American Rose Society as dark red, mauve blend and most recently mauve; the color varies from shades of deep fuschia to dark red depending on the climate and growing conditions; whereas Elizabeth Abler is consistently medium red and much smaller in bloom size.

The single color photographic view shows, in plain view, a bouquet of 'Elizabeth Abler' in various stages of maturity from bud stage to nearly open bloom stage.

The descriptive matter which follows pertains to roses grown and color values observed in plants and newly opened blooms in the months of March through November of 1992. The plants were grown outdoors in Chula Vista, Calif., and are believed to be accurate standards for this cultivar in similar conditions of soil and climate elsewhere.

Referring now specifically to the new and distinct variety of miniature rose plant named 'Elizabeth Abler', the following is a detailed description thereof in outline; all major color plate identifications being by reference to the British Colour Council Horticultural Chart, except where common terms of color definition are employed.

Type: Hardy, dwarf, bushy, greenhouse or outdoor, exhibition or garden decorative potted plant.

Class: Miniature.

Variety name: Elizabeth Abler.

Flowers borne: Usually one to a stem on erect stems with foliage well below the blooms.

Quantity of Bloom: Heavy both outdoors or greenhouse grown.

Bud:

*Peduncle.*—Average length (10 to 15 mm); average diameter and sturdy; ranging from near Scheeles Green (860/3 to 860/1 page 176) with occasional tinting of bronze.

*Hairs.*—Extremely small and sparse with a reddish color; located over the surface of the peduncle and calyx tube.

*Calyx.*—Color range same as peduncle.

*Opening.*—Opens well in all weather.

Bloom:

*Size when fully open.*—Small for a miniature variety (less than 20 mm).

*Petalage.*—Semidouble — 10 to 20 petals, arranged regularly, plus 5 to 10 petaloids.

*Form.*—Urn-shaped to ovoid as the bloom opens. The petals remain somewhat cupped with the apex and/or margins reflexed outward, becoming at maturity more loosely cupped.

Petals: Fairly thick with good substance; both the upper and under surfaces of all petals have a matte finish.

*Shape.*—Outer petals are of a broad obovate form. The inner petals are a broad lanceolate form; and the petaloids are also lanceolate with some occasional irregularities.

Color: Newly opened flowers from plants grown outdoors (March through November of 1992), Chula Vista, Calif.

*Outer petals.*—Ranging from near Currant Red (821/3 to 821 page 167) to near Rose Red (724/3 to 724 page 158).

*Inner petals.*—Ranging from near Crimson (22/2 to 22/1 page 22) to near Rose Madder (23/2 to 23 page 23) Under surfaces — Slightly lighter tones of upper surfaces.

*General color effect.*—Medium red buds and blooms that open to display a slightly paler shade of red on the inner petals. Little to no fading of color throughout the bloom cycle.

*Flower longevity.(March through November 1992).*—Plant in pot 2 to 4 days from bud with sepals reflexed to fully open bloom. Holding at fully opened for 5 to 7 days longer. Cut blooms at living room temperature 7 to 10 days or longer.

Reproductive organs:

*Stamens.*—Arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow with reddish tips.

*Ovaries.*—All encased in calyx.

*Hips.*—Some.

*Seeds.*—1 or 2 in each hip.

*Sepals.*—Permanent; spear-shaped; open as the bloom opens. Occasional foliaceous appendages attractively supplement sepal terminals; these are of varying lengths.

Foliage:

*Leaves.*—5 to 7 leaflets on average; small size for a miniature rose plant.

*Leaflets.*—Broad ovate-shaped.

*Margins.*—Very serrated with tinting of bronze, especially noticeable on the newer foliage.

*Color.*—Ranging from near Spinach Green (0960/3 to 0960 page 187) to near Scheeles Green (860/1 to 860 page 175) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Small in length with average width; tapering auricles angled outward at about 45 degrees.

Growth:

*Habit.*—Dwarf, bush; very compact and low for a miniature rose plant, averaging 20 to 30 cm.

*Rate and character.*—Vigorous and well-branched.

*Canes.*—Medium diameter; sturdy; held erect.

*Main stems.*—Color range same as foliage.

*Thorns.*—Averaging less than 3 to 5 per 5 cm on the main stems and branches. Reddish in color; small size; slender and hooked slightly downward.

*Branches.*—Coloration ranges the same as does that of the foliage.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant, name 'Elizabeth Abler', hardy, dwarf, compact growth, which is vigorous, well-branched and attractive in appearance, substantially as illustrated and described; characterized by its hybrid tea form blooms, ranging from near Currant Red to near Rose Red with inner petals ranging from near Crimson to near Rose Madder with little to no fading of color throughout the bloom cycle. The blooms are microminiature (smaller than the average miniature bloom) and abundant on the bush and usually borne one to a stem.

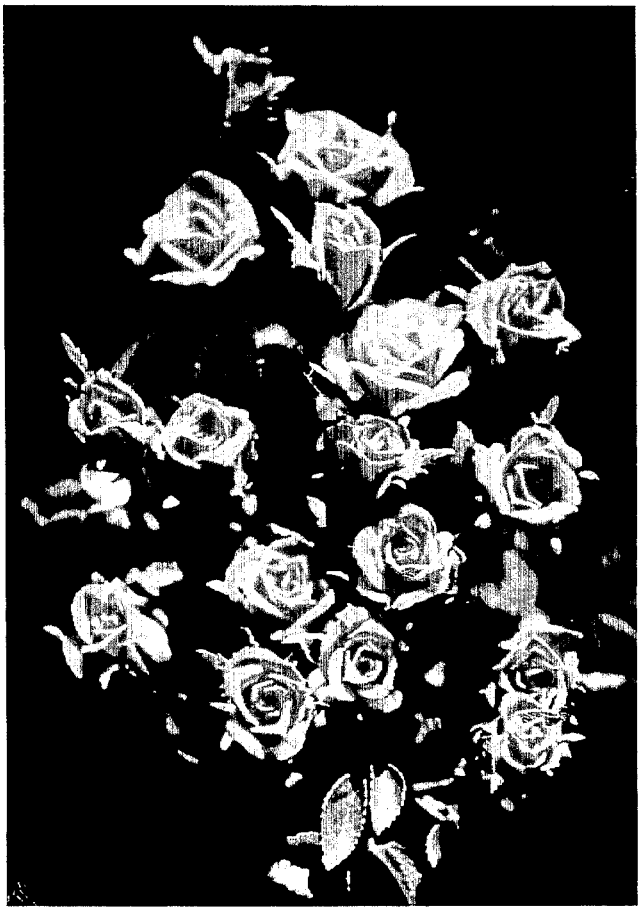

* * * * *